United States Patent
Aruga et al.

(10) Patent No.: US 11,936,737 B2
(45) Date of Patent: Mar. 19, 2024

(54) NOTIFICATION CONTROL APPARATUS, NOTIFICATION CONTROL METHOD, AND NOTIFICATION CONTROL PROGRAM

(71) Applicant: NIPPON TELEGRAPH AND TELEPHONE CORPORATION, Tokyo (JP)

(72) Inventors: Reiko Aruga, Musashino (JP); Hitoshi Seshimo, Musashino (JP); Tae Sato, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 18/022,471

(22) PCT Filed: Aug. 26, 2020

(86) PCT No.: PCT/JP2020/032163
§ 371 (c)(1),
(2) Date: Feb. 21, 2023

(87) PCT Pub. No.: WO2022/044160
PCT Pub. Date: Mar. 3, 2022

(65) Prior Publication Data
US 2023/0328148 A1    Oct. 12, 2023

(51) Int. Cl.
*H04L 29/08* (2006.01)
*H04L 67/12* (2022.01)
*H04L 67/1396* (2022.01)

(52) U.S. Cl.
CPC .......... *H04L 67/1396* (2022.05); *H04L 67/12* (2013.01)

(58) Field of Classification Search
CPC ........................... H04L 67/12; H04L 67/1396
See application file for complete search history.

(56) References Cited

U.S. PATENT DOCUMENTS

2020/0134652 A1*  4/2020 DeLuca ............ G06Q 30/0238
2020/0289055 A1*  9/2020 Vleugels ................ G16H 50/20
(Continued)

FOREIGN PATENT DOCUMENTS

JP    2017000167 A  *  6/2015  ............ G16H 20/30
JP      201953676 A     4/2019
(Continued)

OTHER PUBLICATIONS

PCT Written Opinion PCT-JP2020-032163 (Year: 2021).*
(Continued)

*Primary Examiner* — Boris D Grijalva Lobos
(74) *Attorney, Agent, or Firm* — Harness, Dickey & Pierce, P.L.C.

(57) ABSTRACT

A notification control apparatus according to an embodiment includes: a reception unit that receives movement event information indicating that a movement event of a user has occurred; a schedule presence/absence determination unit that determines whether or not the user has a schedule immediately following or immediately preceding an occurrence time point of the movement event; a message generation unit that generates an advice to be notified to the user on the basis of the determination and the occurrence time point of the movement event; and a presentation unit that presents the generated advice to the user.

5 Claims, 12 Drawing Sheets

(56) References Cited

U.S. PATENT DOCUMENTS

2021/0064664 A1   3/2021  Aruga et al.
2021/0110352 A1*  4/2021  Dunne ............... G06Q 10/1093

FOREIGN PATENT DOCUMENTS

JP      2019159838 A    9/2019
JP      2019185389 A    10/2019

OTHER PUBLICATIONS

MLT Co., Ltd., Health management that can be done with Garmin vol. 1, MLTsports, Jul. 7, 2020 (Reading Day), https://mlt.jpn.com/garmin-healthcare-vol-1/.
Apple Inc., Apple Watch—Complete the Ring, literature, Jul. 7, 2020 (Reading Day), https://www.apple.com/jp/watch/close-your-rings/.
Tadashi Okoshi et al., Attention and Engagement-Awareness in the Wild: A Large-Scale Study with Adaptive Notifications, 2017 IEEE International Conference on Pervasive Computing and Communications (PerCom), Mar. 13, 2017.

* cited by examiner

Fig. 5

| MESSAGE ID | CATEGORY | HOURS | MESSAGE |
|---|---|---|---|
| 1 | EXERCISE | 8:00~11:30 | WALK TO AND FROM THE RESTROOM WHILE MOVING YOUR SHOULDERS IN CIRCLES |
| 2 | EXERCISE | 8:00~11:30 | RAISE YOUR HEELS WHEN WAITING FOR AN ELEVATOR OR THE LIKE |
| ... | ... | ... | ... |
| 100 | EXERCISE | 8:00~11:30 | WALK AT A BRISK PACE TO YOUR DESTINATION |
| 101 | MEAL | 11:30~13:00 | SELECT SOMETHING OTHER THAN FRIED FOOD AT THE CAFETERIA TODAY |
| 102 | MEAL | 11:30~13:00 | BEGIN YOUR MEAL BY TAKING THREE BITES OF VEGETABLES |
| ... | ... | ... | ... |
| 200 | MEAL | 11:30~13:00 | TAKE AT LEAST 20 MINUTES TO ENJOY YOUR MEAL |
| 201 | REST | 13:00~18:00 | TAKE A DEEP BREATH |
| 202 | REST | 13:00~18:00 | THINK ABOUT THREE THINGS TO DO OVER THE WEEKEND THAT WILL MAKE YOU HAPPY |
| ... | ... | ... | ... |
| 300 | REST | 13:00~18:00 | CLOSE YOUR EYES FOR 10 SECONDS AND CONCENTRATE ON YOUR BREATHING |

Fig. 9

| USER ID | PRESENCE OR ABSENCE OF IMMEDIATELY PRECEDING SCHEDULE | NOTIFICATION |
|---|---|---|
| 1 | PRESENT | OK |
| 1 | ABSENT | OK |
| 2 | PRESENT | OK |
| 2 | ABSENT | UNACCEPTABLE |
| 3 | PRESENT | UNACCEPTABLE |
| 3 | ABSENT | OK |
| 4 | PRESENT | UNACCEPTABLE |
| 4 | ABSENT | UNACCEPTABLE |
| ... | ... | ... |

United States Patent US 11,936,737 B2

NOTIFICATION CONTROL APPARATUS, NOTIFICATION CONTROL METHOD, AND NOTIFICATION CONTROL PROGRAM

CROSS-REFERENCE TO RELATED APPLICATIONS

This application is a 371 U.S. National Phase of International Application No. PCT/JP2020/032163, filed on Aug. 26, 2020. The entire disclosure of the above application is incorporated herein by reference.

TECHNICAL FIELD

An aspect of the present invention relates to a notification control apparatus, a notification control method, and a notification control program.

BACKGROUND ART

There is provided a service for notifying a user of advice for urging the user to perform an action for health from a smart phone, a smart watch, or the like.

For example, NPL 1 provides a service for capturing timing at which strong stress continues and promoting deep respiration, and NPL 2 provides a service that prompts a user to stand up and move his/her body when his/her seated state continues.

In addition, NPL 3 reports that, when a push notification is made during a break between actions, a reaction time until the push notification is opened is short and an opening rate of the push notification is high.

Furthermore, in order to prevent overlooking of a push notification and forgetting to execute an action requested by the push notification, PTL 1 proposes presenting a user of a smartphone with a question sentence related to mental health when passing through a door which is a moment having a high possibility of being a break in action in an office.

CITATION LIST

Patent Literature

[PTL 1] Japanese Patent Application Publication No. 2019-185389
Non Patent Literature
[NPL 1] https://mlt.jpn.com/garmin-healthcare-vol-1/
[NPL 2] https://www.apple.com/jp/watch/close-your-rings/
[NPL 3] Attention and Engagement-Awareness in the Wild: A Large-Scale Study with Adaptive Notifications, PerCom 2017

SUMMARY OF INVENTION

Technical Problem

In an office, when a user leaves a seat or leaves a room through a door, the user may intend to take a rest such as using the washroom or going to a concession stand or may intend to move to a conference room in which a nearest event is scheduled.

While there is a method of interlocking with a scheduler of a user terminal in order to grasp an immediately preceding schedule and not notifying an advice when a nearest schedule is present, there are cases where the absence of an API makes it difficult to interlock with the scheduler.

The present invention has been made by paying attention to the circumstances described above and an object thereof is to provide a notification control apparatus, a notification control method, and a notification control program which notify a user of an advice at a timing where it is likely that the user does not have a nearest schedule.

Solution to Problem

In order to solve the above problem, a notification control apparatus according to the present invention includes: a reception unit that receives movement event information indicating that a movement event of a user has occurred; a schedule presence/absence determination unit that determines whether or not the user has a schedule immediately following or immediately preceding an occurrence time point of the movement event; a message generation unit that generates an advice to be notified to the user based on the determination and the occurrence time point of the movement event; and a presentation unit that presents the user with the generated advice.

Advantageous Effects of Invention

According to one aspect of the present invention, a notification control apparatus, a notification control method, and a notification control program can be provided which notify a user of an advice at a timing where it is likely that the user does not have a nearest schedule.

BRIEF DESCRIPTION OF DRAWINGS

FIG. 5 shows an example of a message list stored in a message list storage unit in FIG. 3.
FIG. 9 is a diagram showing an example of user attribute information for each user stored in a server accessible by a user terminal.

DESCRIPTION OF EMBODIMENTS

Hereinafter, an embodiment related to the present invention will be described with reference to the drawings.

[Configuration]

Figure 1:
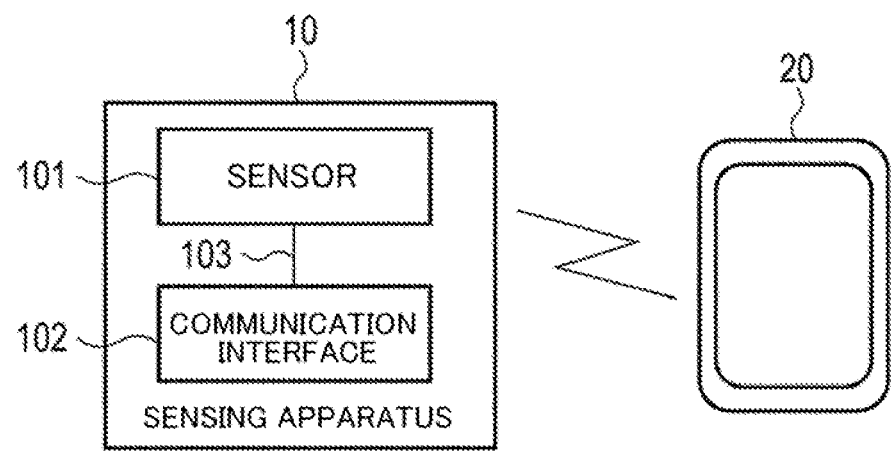
FIG. 1 is a block diagram showing an example of a configuration of a notification control system according to an embodiment of the present invention.

FIG. 1 is a block diagram showing an example of a configuration of a notification control system including a notification control apparatus according to an embodiment of the present invention. The present system includes a sensing apparatus 10 and a user terminal 20 such as a smart phone carried by a user as a notification control apparatus. In addition, although only one user terminal 20 is shown in FIG. 1 for the purpose of simplifying the drawing, the notification control system may include a large number of user terminals.

The sensing apparatus 10 is an apparatus for detecting a movement event of a user and includes a sensor 101 and a communication interface 102. The sensing apparatus 10 is arranged on a seat on which the user sits, on a door to a room in which the user is present, on a floor near the door, or the like. For example, movement events of the user include, but are not limited to, taking or leaving the user's seat or entering or leaving the user's room. Hereinafter, a movement event in which the user leaves the user's seat or leaves the user's room will be referred to as an out-event and a movement event in which the user takes the user's seat or enters the user's room will be referred to as an in-event.

The user terminal 20 is a portable terminal such as a smartphone, a tablet terminal, or a wearable terminal. Furthermore, the user terminal 20 may include a plurality of user terminals. For example, a first user terminal such as a smartphone receives and processes information from the sensing apparatus 10, a base station, or the like and subsequently transmits processed information to a second user terminal such as a wearable terminal. In addition, the second user terminal can display advice to the user on the basis of the received information.

The sensing apparatus 10 and the user terminal 20 are connected by a short-range radio communication technique such as ZigBee (registered trademark), Bluetooth (registered trademark), or wireless LAN. Furthermore, when the user terminal 20 includes a plurality of user terminals, each of the plurality of user terminals can be connected via short-range radio technology or a network. It is needless to say that the user terminal 20 can be connected to a server or the like (not illustrated in FIG. 1) via a network.

The sensor 101 in the sensing apparatus 10 is a sensor for detecting a movement event of the user. The sensor 101 is connected to the communication interface 102 via a bus 103 or by radio. The sensor 101 is a sensor capable of detecting movement of the user such as an acceleration sensor, a pressure sensor, or an infrared sensor. For example, the sensing apparatus 10 can detect a movement event of the user by attaching an acceleration sensor to a chair of the user and detecting a movement of the chair by the acceleration sensor. Although only one sensor 101 is shown in FIG. 1, the sensing apparatus 10 may include a large number of sensors. In addition, the sensor 101 may be disposed inside the sensing apparatus 10 or may be disposed as an apparatus being separate from the sensing apparatus 10.

The communication interface 102 in the sensing apparatus 10 includes a wireless communication module for wirelessly connecting with the user terminal 20 using short-range wireless technology or the like. The communication interface 102 may include a wireless communication module that wirelessly connects with the user terminal 20 via a network. For example, when the sensing apparatus 10 is disposed in the vicinity of a door, the communication interface 102 can detect a movement event of the user by communicating with the user terminal 20 using short-range radio technology. In this case, the sensing apparatus 10 need not have the sensor 101. In addition, the communication interface 10 may include a wireless communication module which is wirelessly connected to the user terminal 20 via a network composed of an IP network including the Internet and an access network for accessing the IP network. In this case, the access network may be a general access network such as a cellular phone network or a wireless LAN.

Figure 2:
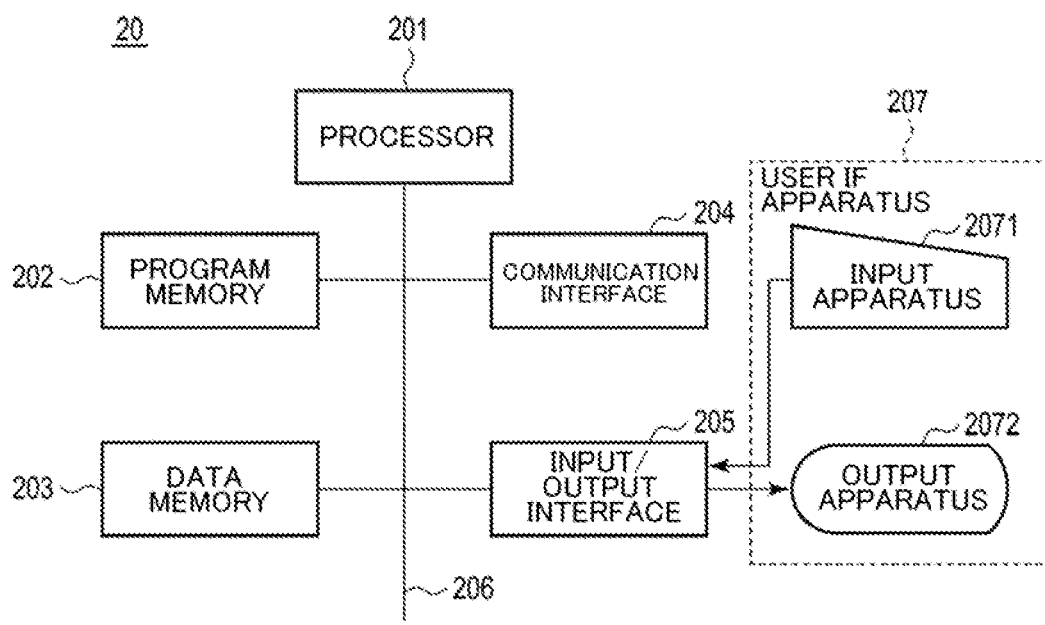
FIG. 2 is a block diagram showing an example of a hardware configuration of a user terminal in FIG. 1.

FIG. 2 is a block diagram showing an example of a hardware configuration of the user terminal 20.

The user terminal 20 has, for example, a hardware processor 201 such as a CPU (Central Processing Unit) or a MPU (Micro Processing Unit). In addition, a program memory 202, a data memory 203, a communication interface 204, and an input/output interface 205 are connected to the processor 201 via a bus 206.

As a storage medium, the program memory 202 can be a combination of a nonvolatile memory such as an EPROM (Erasable Programmable Read Only Memory) or a memory card to and from which data can be written and read at any time and a nonvolatile memory such as a ROM (Read Only Memory). The program memory 202 stores programs that are required to execute various types of processing including a notification control program. In other words, a processing functional unit in each unit of a functional configuration to be described later can be implemented by causing the processor 201 described above to read and execute a program stored in the program memory 202.

The data memory 203 is a storage that uses, as a storage medium, a combination of, for example, a nonvolatile memory such as a memory card to and from which data can be written and read at any time and a volatile memory such as a RAM (Random Access Memory). The data memory 203 is used to store data acquired and generated when the processor 201 executes a program and carries out various types of processing.

The communication interface 204 includes one or more wireless communication modules. For example, the communication interface 204 includes a wireless communication module for wirelessly connecting with the sensing apparatus 10 or another user terminal using short-range wireless technology. Furthermore, the communication interface 204 may include a wireless communication module that wirelessly connects to a Wi-Fi access point or a mobile phone base station. The wireless communication module communicates with the sensing apparatus 10 under the control of the processor 201, and can transmit and receive various kinds of information. Note that the communication interface 204 can include one or more wired communication modules.

The input/output interface 205 is an interface with a user interface apparatus 207. In FIG. 2, the "user interface apparatus" is described as the "user IF apparatus".

The user interface apparatus 207 includes an input apparatus 2071 and an output apparatus 2072. The output apparatus 2072 is a display device using, for example, a liquid crystal, organic EL (Electro Luminescence), or the like and displays an image corresponding to a signal input from the input/output interface 205. The input apparatus 2071 is, for example, an input detection sheet which is disposed on a display screen of a display device that is the output apparatus 2072 and which employs an electrostatic method or a pressure method, and outputs a touch position of the user to the processor 201 via the input/output interface 205.

Although not shown in FIG. 1, it is needless to say that the sensing apparatus 10 may also include a processor, a program memory, and a data memory in a similar manner to the user terminal 20 shown in FIG. 2.

First Embodiment (1) Functional Configuration

Figure 3:
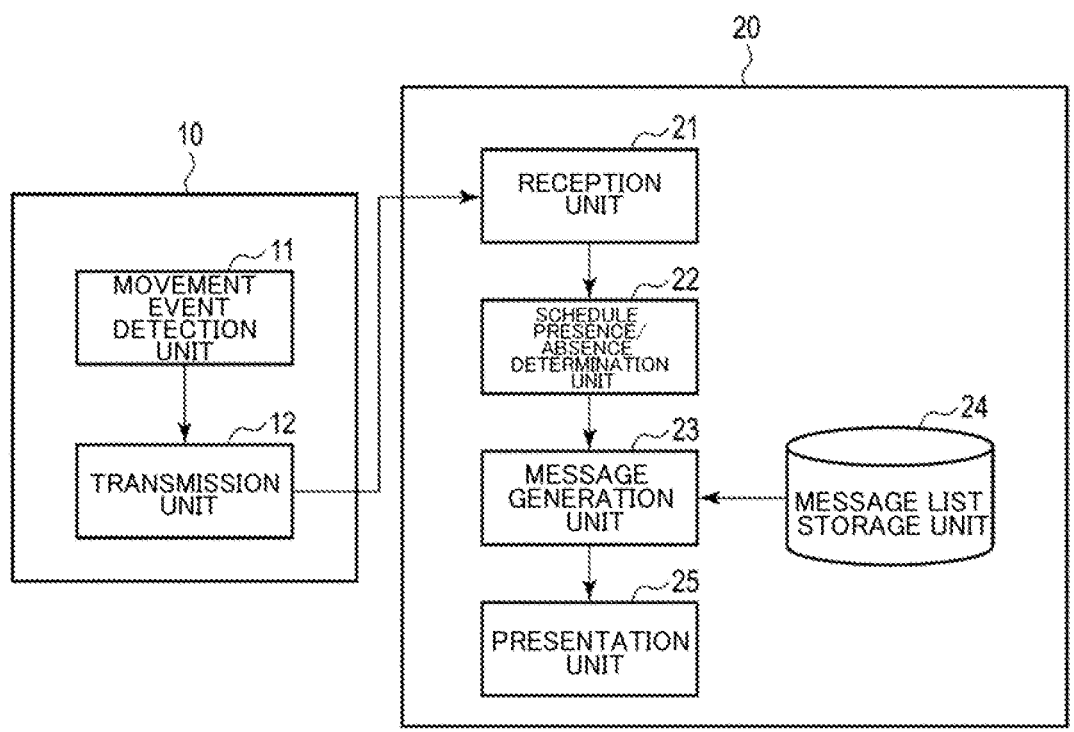
FIG. 3 is a block diagram showing a functional configuration of a sensing apparatus and a user terminal according to a first embodiment.

FIG. 3 is a block diagram showing a functional configuration of the sensing apparatus 10 and the user terminal 20 according to a first embodiment.

The sensing apparatus 10 includes a movement event detection unit 11 and a transmission unit 12.

The movement event detection unit 11 includes the sensor 101 for detecting a movement event of a user or the communication interface 102. For example, when the sensor 101 of the sensing apparatus 10 is disposed on a seat of the user, the movement event detection unit 11 can detect a movement event of the user by detecting a movement of the seat or a change in pressure of a seat surface by the sensor 101. Alternatively, when the sensor 101 of the sensing apparatus 10 is disposed on a door of a room in which the user is present or the communication interface 102 of the sensing apparatus 10 is disposed near the door, the movement event detection unit 11 can detect a movement event of the user by detecting the movement of the door by the sensor 101 or by communicating with the user terminal 20 by the communication interface 102. That is, the movement event detection unit 11 can detect a movement event including an out-event in which the user leaves a seat or leaves the user's room and an in-event in which the user sits on the seat or enters the user's room. In the present embodiment, the movement event detection unit 11 transmits movement information indicating that an out-event or an in-event has occurred to the transmission unit 12.

Figure 4:
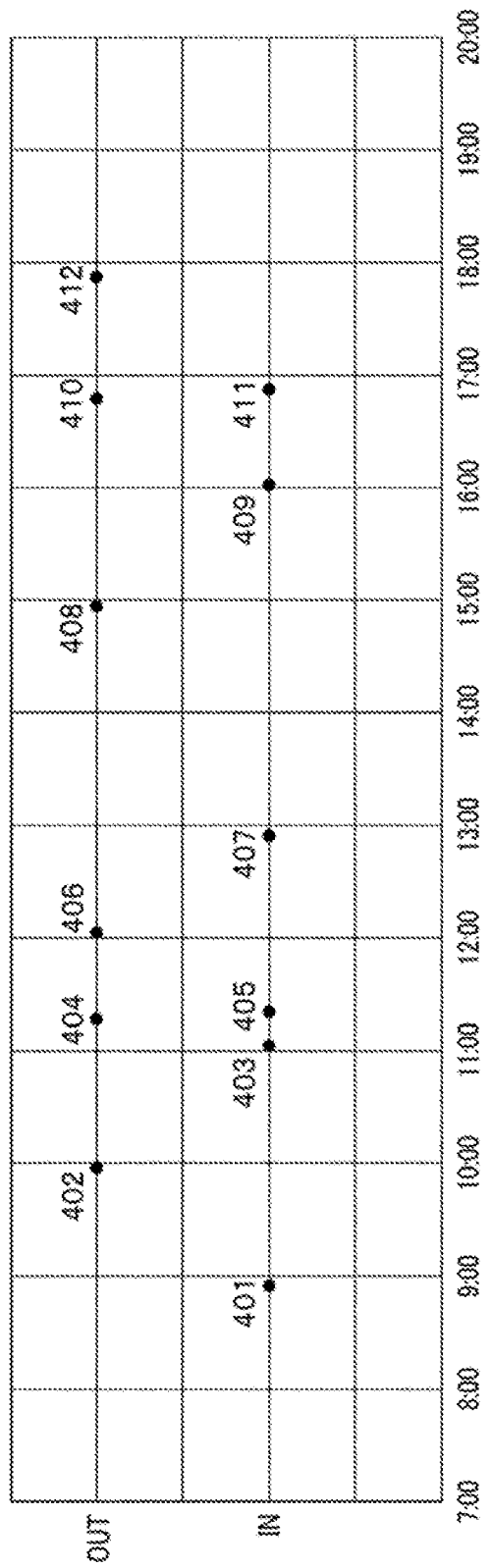
FIG. 4 is a diagram representing time series data of an in-event and an out-event detected by a movement event detection unit in FIG. 3.

FIG. 4 shows time series data of an in-event and an out-event detected by the movement event detection unit 11. In FIG. 4, an x-axis represents time and a y-axis represents whether an in-event has occurred or an out-event has occurred. In FIG. 4, an occurrence of an in-event is indicated by IN and an occurrence of an out-event is indicated by OUT. In the example shown in FIG. 4, it is shown that an in-event occurs at points 401, 403, 405, 407, 409 and 411 and an out-event occurs at points 402, 404, 406, 408, 410 and 412. In the present embodiment, every time an out-event or an in-event occurs, the movement event detection unit 11 is to transmit movement information indicating which movement event has occurred to the transmission unit 12.

The transmission unit 12 determines which of an out-event and an in-event has occurred on the basis of the movement information transmitted from the movement event detection unit 11. When it is determined that an out-event has occurred, the transmission unit 12 generates movement event information including a movement flag indicating that an out-event has occurred and transmits the movement event information to the user terminal 20. As a 1-bit flag, the movement flag is capable of indicating an occurrence of an out-event by, for example, assuming a value of "1". However, since movement event information itself is not generated when an out-event has not occurred, there is no particular need to distinguish between movement flag values of "0" and "1".

The user terminal 20 includes a reception unit 21, a schedule presence/absence determination unit 22, a message generation unit 23, a message list storage unit 24, and a presentation unit 25.

The reception unit 21 receives movement event information transmitted from the sensing apparatus 10. In accordance with the reception of the movement event information, the reception unit 21 generates a current time point as a time stamp at the time point of occurrence of an out-event and transmits the generated time stamp to the schedule presence/absence determination unit 22.

The schedule presence/absence determination unit 22 determines whether or not there is a schedule immediately following the movement event on the basis of the time point indicated by the time stamp received from the reception unit 21. When it is determined that there is no schedule immediately following the movement event, the schedule presence/absence determination unit 22 transmits a message generation instruction including an instruction to generate a message and a time stamp to the message generation unit 23.

When receiving the message generation instruction from the schedule presence/absence determination unit 22, the message generation unit 23 refers to the time stamp included in the message generation instruction and a message list stored in the message list storage unit 24 and generates message information including a message being an advice to be displayed to the user. Subsequently, the message generation unit 23 transmits the generated message information to the presentation unit 25.

The message list storage unit 24 stores a message list corresponding to time.

FIG. 5 shows an example of a message list stored in the message list storage unit 24. In the example shown in FIG. 5, message ID 1 to message ID 100 store a message corresponding to the time from 8:00 to 11:30. In addition, message ID 101 to message ID 200 store a message corresponding to the time from 11:30 to 13:00 and message ID 201 to message ID 300 store a message corresponding to the time from 13:00 to 18:00. Furthermore, although not illustrated, it is needless to say that the user can create a message through the user interface apparatus 207 of the user terminal 20 and store the message as a message list. Moreover, the message list shown in FIG. 5 is a mere example, and it is needless to say that it is possible to store messages corresponding to categories or the like or to store additional information if necessary.

The presentation unit 25 presents the user with advice through the user interface apparatus 207 by, for example, a push notification on the basis of the message information transmitted from the message generation unit 23.

(2) Operations

Operations of the user terminal 20 as a notification control apparatus according to the first embodiment will now be described.

Figure 6:
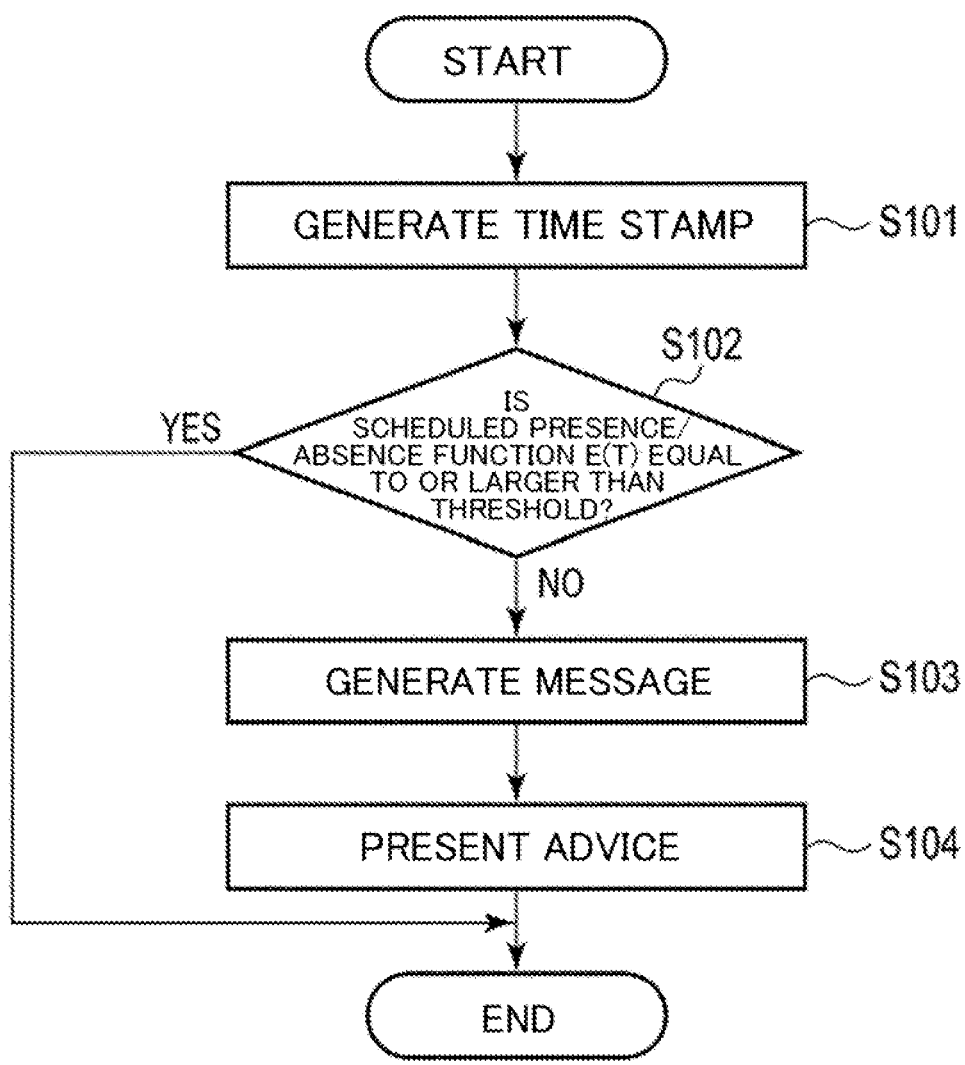
FIG. 6 is an operation flowchart of a notification control apparatus according to the first embodiment.

FIG. 6 is an operation flowchart of the notification control apparatus. The operations shown in the flowchart are realized when the processor 201 of the user terminal 20 reads and executes the notification control program stored in the program memory 202. It is assumed that the flowchart is started every time the user terminal 20 receives movement event information from the sensing apparatus 10.

That is, when the reception unit 21 of the user terminal 20 receives, from the sensing apparatus 10, movement event information including a movement flag indicating that an out-event indicating that the user has left the user's seat or the user has left the user's room has occurred, the reception unit 21 generates a time stamp from the current time point (step S101). In addition, the reception unit 21 transmits the time stamp to the schedule presence/absence determination unit 22.

The schedule presence/absence determination unit 22 applies a time point t indicated by the time stamp received from the reception unit 21 to a schedule presence/absence function e(t) stored in advance and determines whether the obtained value is equal to or larger than a threshold or not (step S102). The schedule presence/absence determination unit 22 determines whether or not a schedule exists immediately following the movement event by determining whether or not the value of the schedule presence/absence function e(t) at the time point t indicated by the received time stamp is equal to or larger than the threshold. When it is determined that the value of the schedule presence/absence function e(t) is equal to or larger than the threshold, that is, when it is determined that there is a schedule immediately following the event, the user terminal 20 does not notify the user of the message and the processing is terminated. Alternatively, when the value of the schedule presence/absence function e(t) is smaller than the threshold, that is, when it is determined that there is no schedule immediately following the movement event, the schedule presence/absence determination unit 22 transmits a message generation instruction including a time stamp to the message generation unit 23. The message generation instruction may include a message ID.

Figure 7:
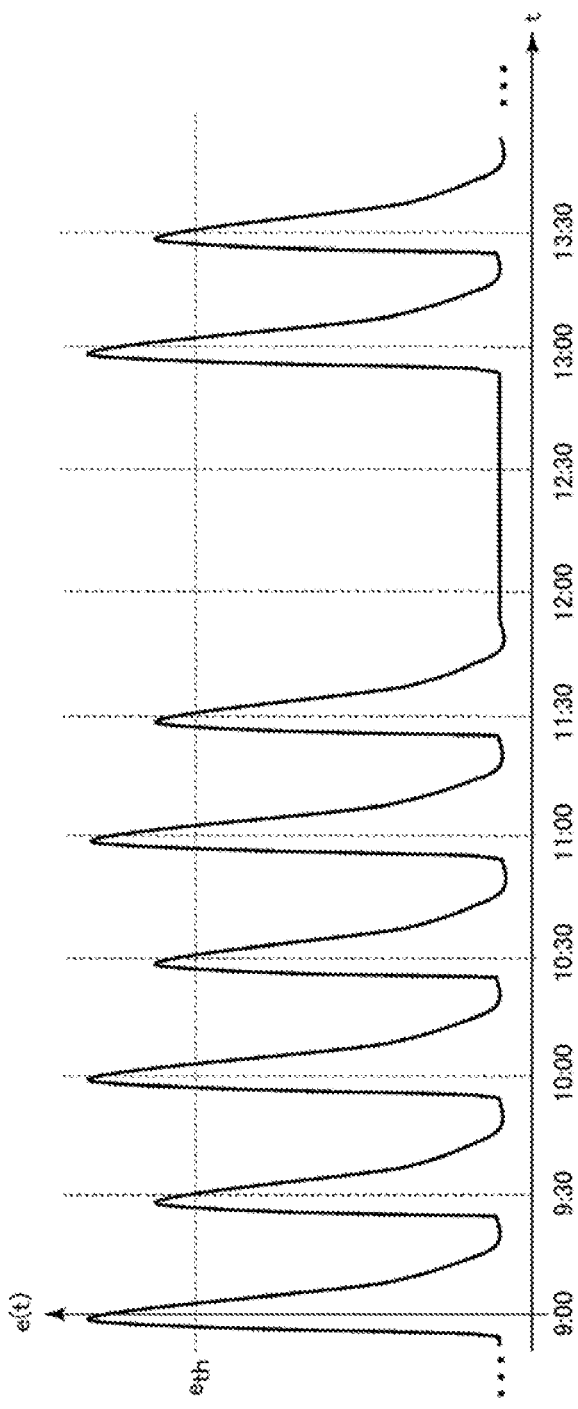
FIG. 7 is a diagram showing an example of a schedule presence/absence function $e(t)$.

FIG. 7 shows an example of the schedule presence/absence function e(t). In FIG. 7, an x-axis represents time and a y-axis represents a value of the schedule presence/absence function e(t). In addition, $e_{th}$ on the y-axis represents a threshold. In this case, it is assumed that the schedule presence/absence function e(t) is determined under the following premise.

When the user works in an office, many schedules start on the hour or the half hour such as schedules starting at 13:00 or schedules starting at 14:30. When the user moves from a seat for performing normal business to a place for an event such as a scheduled conference, an out-event occurs where the user leaves the seat or leaves the user's room. A time point at which the out-event occurs is often several minutes before a start time point of an event such as five minutes before the start time point of the event. In general, since the user moves in time for a scheduled time point, a distribution of the out-event is usually such that a peak appears several minutes before the start time point of the event such as between 55 minutes to 60 minutes after every hour (in other words, on the next hour) or between 25 minutes to 30 minutes after the hour. Therefore, the out-event has a higher probability of occurrence before the start time point of an event than after the start time point of the event. That is, there is a high possibility that a movement event for going to an event such as a conference occurs approximately between 25 minutes to 30 minutes after every hour and between 55 minutes to 60 minutes after every hour.

From the above, the schedule presence/absence function e(t) shown in FIG. 7 is a function which selects a prescribed number of minutes (in the present embodiment, 5 minutes) before every hour or every half hour during which an out-event for an event such as a conference is highly likely to occur and in which a waveform of a gamma distribution-like shape repetitively peaks between 25 minutes to 30 minutes after every hour and between 55 minutes to 60 minutes after every hour. In addition, the threshold $e_{th}$ is set such that a value of the schedule presence/absence function e(t) exceeds the threshold $e_{th}$ near the peaks. However, the reason that the schedule presence/absence function e(t) exhibits the behavior shown in FIG. 7 is because time slots are taken into consideration in which conferences are frequently performed and, therefore, the possibility of a schedule being set is low. In view of time slots in which a schedule is set, there are time slots in which a schedule is less likely to be set such as a time slot in the early morning, a time slot corresponding to a lunch break, and a time slot in the night, and such time slots are to be set as schedule-free time slots and a schedule-free time is handled as though there are no schedules. For example, it is assumed that no schedules start at 12:00 and 12:30 and, therefore, there are no peaks immediately preceding 12:00 and 12:30. Furthermore, with respect to the schedule presence/absence function e(t), a model may be determined in advance as described herein or modeling may be performed from an action log of the user and a model may be determined based on a result of the modeling.

Referring to FIGS. 4 and 7, the value of the schedule presence/absence function e(t) at points 404 and 410 in FIG. 4 is smaller than the threshold $e_{th}$. In addition, since point 406 is an out-event for lunch, the value of the schedule presence/absence function e(t) at point 406 is also lower than the threshold $e_{th}$. Furthermore, the value of the schedule presence/absence function e(t) at point 402 indicating an out-event occurring immediately preceding 10 o'clock and point 408 indicating an out-event occurring immediately preceding 15 o'clock is equal to or larger than the threshold $e_{th}$.

When the value of the schedule presence/absence function e(t) corresponding to the time point t indicated by the time stamp is equal to or larger than the threshold $e_{th}$, since an out-event has conceivably occurred due to the user heading toward an event, the user terminal 20 ends processing without generating a message. When the value of the schedule presence/absence function e(t) corresponding to the time point t indicated by the time stamp is smaller than the threshold $e_{th}$, an out-event has conceivably occurred due to a reason other than the user heading toward an event. That is, when this out-event occurs, the schedule presence/absence determination unit 22 is to transmit a message generation instruction to the message generation unit 23.

The message generation unit 23 generates a message on the basis of the message generation instruction (step S103). The message generation unit 13 refers to the time stamp included in the message generation instruction and acquires a message from a message list corresponding to a time including the time point indicated by the time stamp. The acquisition of the message may be performed in the order of message IDs or an arbitrary message may be acquired at random. Alternatively, when the message generation instruction includes a message ID, a message corresponding to the message ID may be acquired. Furthermore, the message generation unit 13 may preferentially acquire a message generated in advance by the user.

The message generation unit 23 transmits message information including the acquired message to the presentation unit 25.

The presentation unit 25 presents the message to the user as an advice (step S104). The presentation unit 25 notifies, by a push notification, the user of the message included in the message information received from the message generation unit 23 as advice. A presentation unit 16 can present advice to the user by the output apparatus 2072 of the user interface apparatus 207. For example, in an out-event at point 404 in FIG. 4, the presentation unit 25 push-notifies an advice "Walk to and from the restroom while moving your shoulders in circles" corresponding to the message ID 1 in FIG. 5 and prompts the user to perform an action corresponding to the advice.

(3) Operational Effect

According to the embodiment described above, the user terminal 20 does not require information on other applications from a scheduler or the like and avoids presenting advice to the user until there is a schedule immediately following a movement event. In addition, when there is no schedule immediately following a movement event, the user terminal 20 enables advice to be presented. Accordingly, the possibility that the user overlooks advice due to being in a hurry to head for an event is reduced. Furthermore, since the user is notified of the advice at a timing where there is a high possibility that there is no schedule immediately following a movement event, the likelihood that the user can take time to carry out the advice increases.

Second Embodiment (1) Functional Configuration

Figure 8:
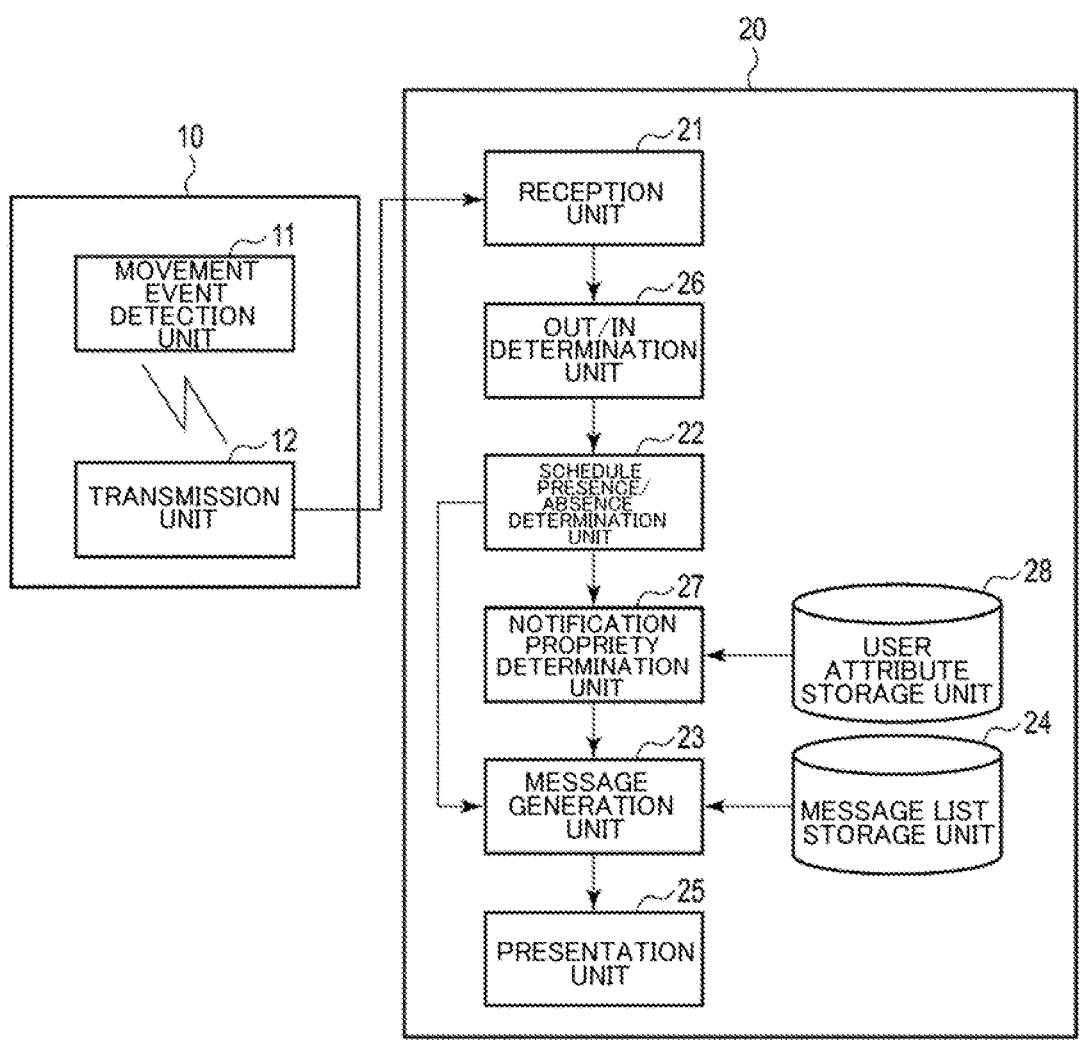
FIG. 8 is a block diagram showing a functional configuration of a sensing apparatus and a user terminal according to a second embodiment.

FIG. 8 is a block diagram showing a functional configuration of the sensing apparatus 10 and the user terminal 20 according to a second embodiment.

As in the first embodiment, the movement event detection unit 11 transmits movement information indicating that an out-event or an in-event has occurred to the transmission unit 12.

The transmission unit 12 determines whether the occurred movement event is an out-event or an in-event on the basis of the received movement information. The transmission unit 12 generates movement event information including an entry/exit movement flag indicating the determination result, and transmits the movement event information to the user terminal 20. For example, as a 1-bit flag, the entry/exit movement flag is capable of indicating an occurrence of an out-event by assuming a value of "1" and indicating an occurrence of an in-event by assuming a value of "0".

The user terminal 20 includes the reception unit 21, an out/in determination unit 26, the schedule presence/absence determination unit 22, a notification propriety determination unit 27, a user attribute storage unit 28, the message generation unit 23, the message list storage unit 24, and the presentation unit 25.

The reception unit 21 receives movement event information transmitted from the sensing apparatus 10. The reception unit 21 generates a time stamp indicating a time point when a movement event is received, and transmits the time stamp together with the received movement event information to the out/in determination unit 26.

The out/in determination unit 26 determines whether the movement event of the user is an out-event or an in-event on the basis of an entry/exit movement flag included in the movement event information transmitted from the reception unit 21. The out/in determination unit 26 transmits out/in determination information indicating a determination result and the time stamp received from the reception unit 21 to the schedule presence/absence determination unit 22.

When the out/in determination information received from the out/in determination unit 26 indicates that the user's movement event is an out-event, the schedule presence/absence determination unit 22 determines whether or not there is a schedule immediately following the movement event on the basis of a time t indicated by the time stamp. When it is determined that there is no event immediately following the movement event, the schedule presence/absence determination unit 22 transmits a message generation instruction including a time stamp and an instruction to generate a message to the message generation unit 23. In addition, when the out/in determination information received from the out/in determination unit 26 indicates that the movement event of the user is an in-event, the schedule presence/absence determination unit 22 determines whether or not a schedule has been present immediately preceding the movement event on the basis of the time point t indicated by the time stamp. The schedule presence/absence determination unit 22 transmits schedule determination information including the determination result and a time stamp to the notification propriety determination unit 27.

The notification propriety determination unit 27 determines whether or not it is good timing to perform a notification to the user on the basis of the schedule determination information and information of a user attribute stored in the user attribute storage unit 28. When it is determined that it is good timing to perform a notification to the user, the notification propriety determination unit 27 transmits a message generation instruction including a time stamp and an instruction to generate a message to the message generation unit 23.

When an in-event occurs, the user attribute storage unit 28 stores, as user attribute information, whether or not advice can be notified on the basis of the presence/absence of an immediately preceding schedule.

In this case, an in-event among the user's movement events is a timing at which the user returns to the user's seat to perform normal business. When push-notifying advice to users at this timing, each user who receives the advice will have a different impression. For example, there is a user who wouldn't mind receiving a push-notification of an advice at a seating timing but there is also a user who feels that a push-notification of an advice at a seating timing is troublesome because the user is already thinking about work after sitting down. Since such perceptions differ from one user to the next, the user terminal 20 must have the user provide input in advance in relation to whether or not the user can be notified of a message when the user takes the user's seat or enters the user's room according to the presence or absence of an immediately preceding schedule and the user terminal 20 must store user attribute information being a result of the input.

The user terminal 20 can communicate with a server (not shown in FIG. 1) via a network and transmit information on a user ID and a user attribute of the user terminal 20. The server can store a user ID and user attribute information. In addition, the user attribute storage unit 28 can also store user attribute information about the user of the user terminal 20 received from the server at an arbitrary timing. It is needless to say that the user terminal 20 may only store the user attribute information input by the user in the user attribute storage unit 28 without transmitting the user attribute information to the server.

FIG. 9 shows an example of user attribute information for each user stored in the server. For example, the user with a user ID 2 prefers to be notified upon return after a nearest event but prefers not to be notified upon return from a break or the like. In addition, the user with a user ID 3 prefers not to be notified upon return after a nearest event but prefers to be notified upon return from a break or the like.

Since the message generation unit 23, the message list storage unit 24, and the presentation unit 25 have the same functional configurations as those of the first embodiment, descriptions thereof will be omitted.

(2) Operations

Operations of a notification control system including the user terminal 20 as a notification control apparatus according to the second embodiment will now be described.

Figure 10:
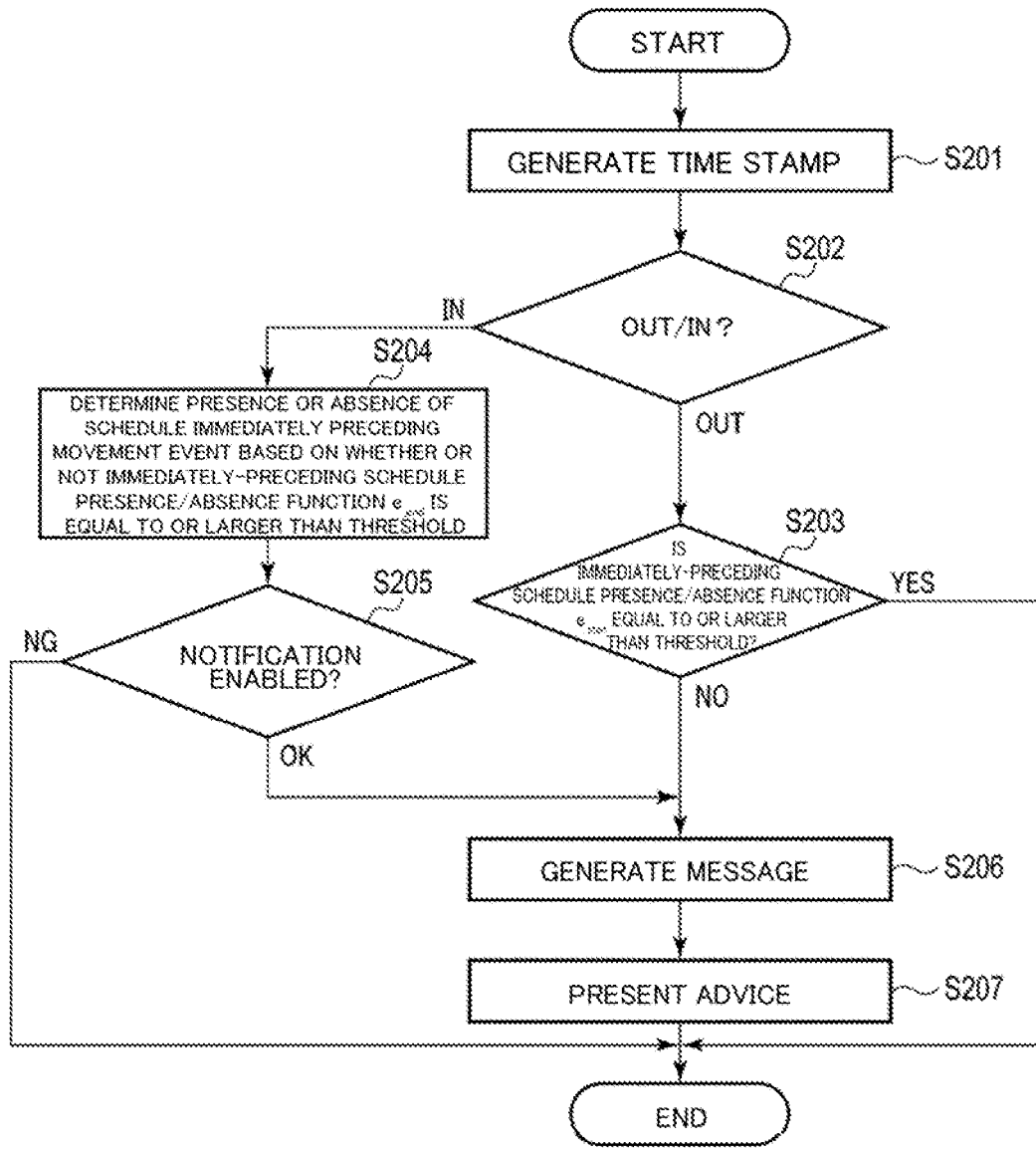
FIG. 10 is an operation flowchart of a notification control apparatus according to the second embodiment.

FIG. 10 is an operation flowchart of the notification control apparatus according to the second embodiment. The operations shown in the flowchart are realized when the processor 201 of the user terminal 20 reads and executes a notification control program stored in the program memory 202. It is assumed that the flowchart is started every time the user terminal 20 receives movement event information from the sensing apparatus 10.

When the reception unit 21 of the user terminal 20 receives movement event information including an entry/exit movement flag transmitted from the sensing apparatus 10, the reception unit 21 generates a time stamp indicating a time point when the movement event is received and transmits the time stamp together with the received movement event information to the out/in determination unit 26 (step S201).

The out/in determination unit 26 determines whether the movement event of the user is an out-event or an in-event on the basis of an entry/exit flag included in the movement event information transmitted from the reception unit 21 (step S202). When the out/in determination unit 26 determines that the movement event of the user is an out-event, the out/in determination unit 26 transmits out-determination information indicating that the movement event of the user is an out-event and a time stamp to the schedule presence/absence determination unit 22 and the flow chart proceeds to step S203. Alternatively, when the out/in determination unit 26 determines that the movement event of the user is an in-event, the out/in determination unit 26 transmits in-determination information indicating that the movement event of the user is an in-event and a time stamp to the schedule presence/absence determination unit 22 and the flow chart proceeds to step S204.

When the schedule presence/absence determination unit 22 receives out-determination information from the out/in determination unit 26, the schedule presence/absence determination unit 22 applies a time point t indicated by the time stamp to an immediately-following schedule presence/absence function $e_{\_start}(t)$ which is stored in advance and which indicates whether or not an event exists immediately following a movement event and determines whether or not the obtained value is equal to or larger than a threshold (step S203). The schedule presence/absence determination unit 22 determines whether or not a schedule exists immediately following a movement event by determining whether or not the value of the immediately-following schedule presence/absence function $e_{\_start}(t)$ at the time point t indicated by the received time stamp is equal to or larger than the threshold.

Figure 11:
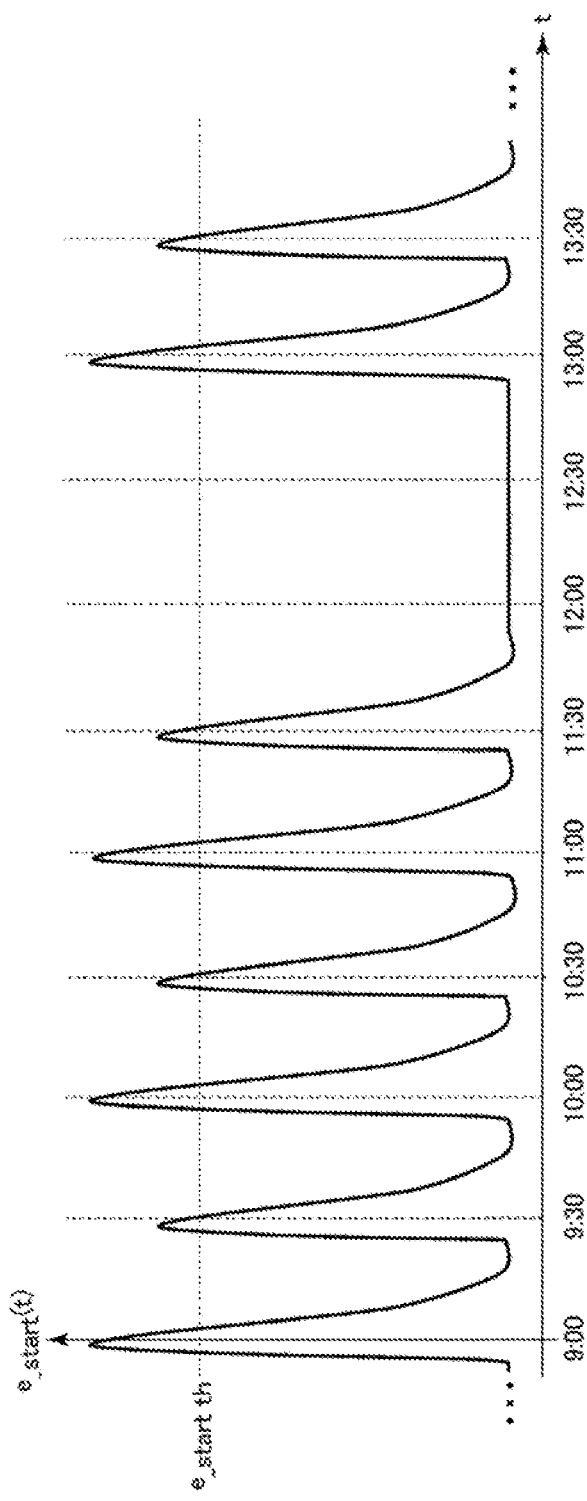
FIG. 11 is a diagram showing an example of an immediately-following schedule presence/absence function $e_{start}(t)$.

FIG. 11 shows an example of the immediately-following schedule presence/absence function $e_{\_start}(t)$. In FIG. 11, an x-axis represents time and a y-axis represents the value of the immediately-following schedule presence/absence function $e_{\_start}(t)$. Furthermore, $e_{\_start\_th}$ on the y-axis represents an immediately-following threshold. As is apparent from FIG. 11, the immediately-following schedule presence/absence function $e_{\_start}(t)$ has a shape similar to that of the schedule presence/absence function e(t) shown in FIG. 7 and the immediately-following threshold $e_{\_start\_th}$ is also similar to the threshold $e_{th}$ described in the first embodiment. Therefore, the description of the immediately-following schedule presence/absence function $e_{\_start}(t)$ will be omitted.

When the immediately-following schedule presence/absence function $e_{\_start}(t)$ at the time point indicated by the time stamp is equal to or larger than the immediately-following threshold $e_{\_start\_th}$, it is determined that an event is "present" immediately following the movement event. Therefore, the user terminal 20 ends processing without generating a message. When the immediately-following schedule presence/absence function $e_{\_start}(t)$ at the time point indicated by the time stamp is smaller than the immediately-following threshold $e_{\_start\_th}$, it is determined that an event is "absent" immediately following the movement event. Therefore, the schedule presence/absence determination unit 22 transmits a message generation instruction including an instruction to generate a message and a time stamp to the message generation unit 23.

On the other hand, when the schedule presence/absence determination unit 22 receives in-determination information from the out/in determination unit 26, the schedule presence/absence determination unit 22 determines whether or not an event had existed immediately preceding a movement event by applying a time point t indicated by the time stamp to an immediately-preceding schedule presence/absence function $e_{\_end}(t)$ which is stored in advance and which indicates whether or not an event had existed immediately preceding a movement event and determining whether or not the obtained value is equal to or larger than a threshold (step S204).

Figure 12:
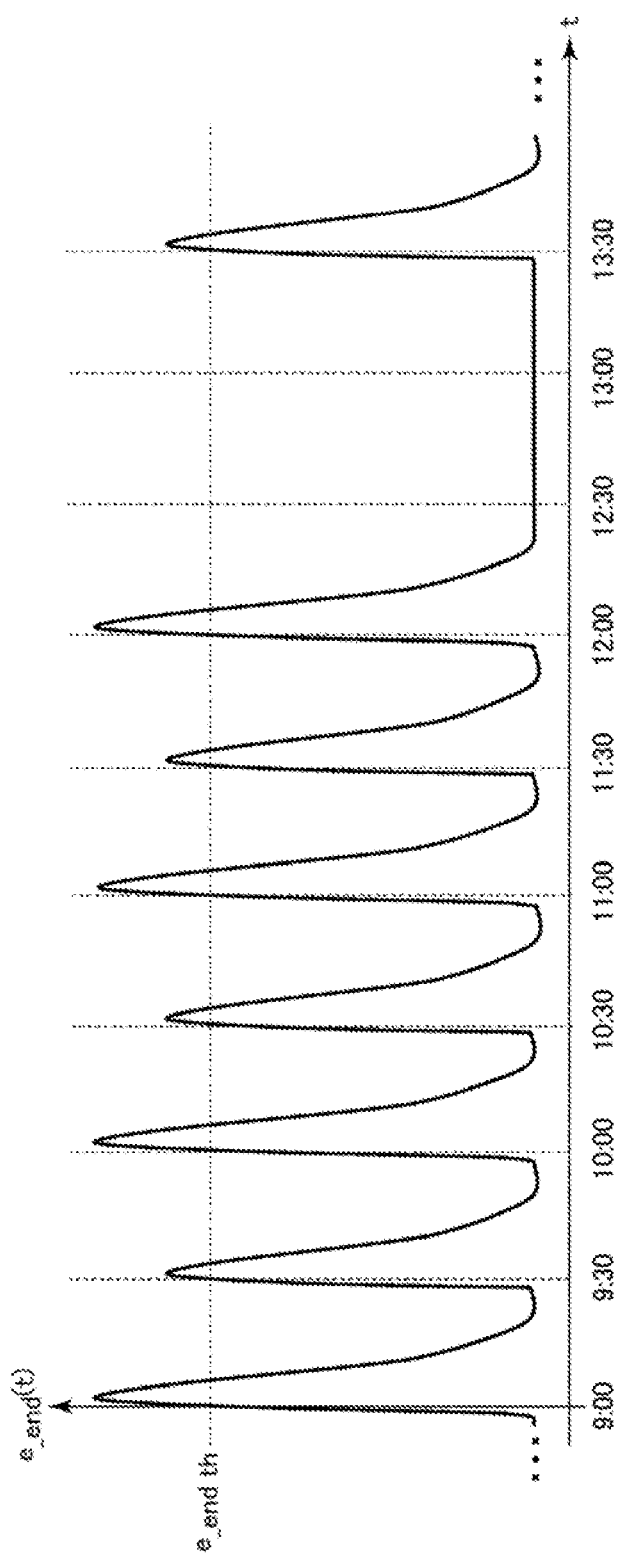
FIG. 12 is a diagram showing an example of an immediately-preceding schedule presence/absence function $e_{end}(t)$.

FIG. 12 shows an example of the immediately-preceding schedule presence/absence function $e_{\_end}(t)$. In FIG. 12, an x-axis represents time and a y-axis represents a value of the immediately-preceding schedule presence/absence function $e_{\_end}(t)$. Furthermore, $e_{\_end\_th}$ to on the y-axis represents an immediately-preceding threshold. The immediately-preceding schedule presence/absence function $e_{\_end}(t)$ is a function in which a waveform of a gamma distribution-like shape is repeated in a similar manner to the immediately-following schedule presence/absence function $e_{\_start}(t)$. Here, it is assumed that the immediately-preceding schedule presence/absence function $e_{\_end}(t)$ is determined under the following premise.

When returning to the user's own seat for performing normal business from a venue of a conference, conceivably, a time point of the return is often several minutes after an end time point of the conference. That is, when an in-event involving entering a user's room occurs between 0 minutes and 5 minutes after every hour or between 30 minutes and 35 minutes after every hour, the in-event is likely to be a movement of return from an event of which a time point had been set such as a conference. That is, an in-event of returning from an event is likely to occur generally between 30 minutes and 35 minutes after every hour and between 0 minutes and 5 minutes after every hour.

From the above, the immediately-preceding schedule presence/absence function $e_{\_end}(t)$ shown in FIG. 12 is a function in which a waveform of a gamma distribution-like shape having peaks between approximately 0 minutes to 5 minutes after every hour and 30 minutes to 35 minutes after every hour is repeated. In addition, the immediately-preceding threshold $e_{\_end\_th}$ is set such that the value of the immediately-preceding schedule presence/absence function $e_{\_end}(t)$ exceeds the immediately-preceding threshold $e_{\_end\_th}$ when near the peaks. However, the reason that the immediately-preceding schedule presence/absence function $e_{\_end}(t)$ exhibits the behavior shown in FIG. 12 is because time slots in which the possibility of setting a schedule is low are taken into consideration. In view of time slots in which a schedule is set, there are time slots in which a schedule is less likely to be set such as a time slot in the early morning, a time slot corresponding to a lunch break, and a time slot in the night, and such time slots are to be set as schedule-free time slots and a schedule-free time is handled as though there are no schedules. For example, it is assumed that no schedules end at 12:30 and 13:00 and, therefore, there are no peaks immediately following 12:30 and 13:00. Furthermore, with respect to the immediately-preceding schedule presence/absence function $e_{\_end}(t)$, a model may be determined in advance as described herein or modeling may be performed from an action log of the user and a model may be determined based on a result of the modeling.

When the value of the immediately-preceding schedule presence/absence function $e_{\_end}(t)$ corresponding to the time point indicated by the time stamp is equal to or larger than the threshold $e_{\_end\_th}$ the schedule presence/absence determination unit 22 determines that an immediately-preceding event is "present" since it is conceivable that the in-event has occurred because the user had returned from the event. When the value of the immediately-preceding schedule presence/absence function $e_{\_end}(t)$ corresponding to the time point indicated by the time stamp is smaller than the immediately-preceding threshold $e_{\_end\_th}$ the schedule presence/absence determination unit 22 determines that an immediately-preceding event is "absent" since it is conceivable that the in-event has occurred because the user had returned from a break or the like. The schedule presence/absence determination unit 22 transmits schedule determination information including information indicating the determination result and a time stamp to the notification propriety determination unit 27.

The notification propriety determination unit 27 determines whether or not it is good timing to perform a notification to the user on the basis of information indicating a determination result in the schedule determination information and the user attribute information stored in the user attribute storage unit 28 (step S205). For example, when the information indicating the determination result indicates "present", the notification propriety determination unit 27 refers to "present" of the user attribute information stored in the user attribute storage unit 28. In addition, the notification propriety determination unit 27 determines whether a notification is "OK" or "unacceptable" when an immediately preceding schedule is "present". If "OK", the notification propriety determination unit 27 transmits a message generation instruction including a time stamp to the message generation unit 23. On the other hand, in the case of "unacceptable", the user terminal 20 ends the processing without generating a message.

The message generation unit 23 generates a message on the basis of the message generation instruction (step S206). Since an operation of step S206 is the same as that in step S103 of the first embodiment, a description thereof will be omitted.

The presentation unit 25 presents the message generated by the message generation unit 13 to the user as advice (step S207). Since an operation of step S207 is the same as that in step S104 of the first embodiment, a description thereof will be omitted.

(3) Operational Effect

According to the embodiment described above, the user terminal 20 does not require information on other applications from a scheduler or the like and can avoid presenting advice to the user until there is a schedule immediately following a movement event. Accordingly, the user can reduce the possibility of overlooking advice due to being in a hurry to head for a nearest event. Furthermore, since the user is notified of the advice at a timing where there is a high possibility that there is no schedule immediately following a movement event, the likelihood that the user can take time to carry out the advice increases. Furthermore, according to the embodiment described above, it is possible to notify the user of an advice depending on whether or not there is a schedule immediately preceding the movement event. Therefore, when the user returns to the user's own seat, the advice can be presented to the user according to the user's preference. As a result, since the advice is presented at the timing preferred by the user, the possibility of overlooking the advice is reduced.

Other Embodiments

Note that the present invention is not limited to the embodiments described above.

For example, in FIG. 10, the step S205 can be omitted. In this case, the user device may be changed such that, when the schedule presence/absence determination unit 22 determines that there is no schedule immediately preceding a movement event in the determination in step S204, the user device notifies the user of advice, and when the schedule presence/absence determination unit 22 determines that there is a schedule immediately preceding the movement event, the user device ends the processing without notifying the advice. That is, the present embodiment can also be configured to not use user attribute information. This is effective when user attribute information has not been obtained from the user.

Although the present embodiment has been described on the assumption that the user works in an office, the present invention is not limited to such a case. For example, the user may be an inpatient at a hospital. In this case, a configuration can be adopted in which advice is not notified when leaving a patient room to undergo an examination or the like but advice is notified when leaving the patient room for purposes other than an examination.

While the prescribed number of minutes set to 5 minutes in the embodiment described above, it is needless to say that the present invention is not limited thereto. The prescribed number of minutes may be set arbitrarily by the user. This applies likewise to schedule-free time slots.

Although a time stamp is generated by the reception unit 21 of the user terminal 20 in the above embodiments, a time stamp may be generated by the schedule presence/absence determination unit 22 or the out/in determination unit 26 or a time stamp may be generated on the side of the sensing apparatus 10 and included in movement information to be transmitted to the user terminal 20.

Also, the methods described in the embodiments can be stored, as a program (software means) that can cause a computing machine (computer) to execute it, in a recording medium such as a magnetic disk (such as a floppy (registered trademark) disk or a hard disk), an optical disk (such as a CD-ROM, a DVD, or an MO), or a semiconductor memory (such as a ROM, a RAM, or a flash memory), or can be transmitted and distributed by a communication medium. Note that programs stored on a medium side also include a setting program for configuring, in the computer, the software means (including not only an execution program but also a table and a data structure) to be executed by the computer. The computer implementing the present apparatus executes the processing described above by reading a program recorded in a recording medium or building the software means using the setting program in some cases and allowing the software means to control an operation of the computer. Note that the recording medium as referred to in the present specification is not limited to a recording medium for distribution, and includes a storage medium provided in the computer or in a device connected thereto via a network, such as a magnetic disc or a semiconductor memory.

In short, the present invention is not limited to the above-described embodiments, and can be variously modified at the implementation stage without departing from its spirit and scope. Also, the embodiments may be appropriately combined, to the greatest extent possible, to obtain combined effects. Furthermore, the above-described embodiments include inventions in various stages, and various inventions can be extracted through appropriate combinations of a plurality of disclosed constituent elements.

REFERENCE SIGNS LIST

10 Sensing apparatus
11 Movement event detection unit
12 Transmission unit
13 Message generation unit
16 Presentation unit
20 User terminal
21 Reception unit
22 Schedule presence/absence determination unit
23 Message generation unit
24 Message list storage unit
25 Presentation unit
26 Out/in determination unit
27 Notification propriety determination unit
28 User attribute storage unit
101 Sensor
102 Communication interface
103 Bus
201 Processor
202 Program memory
203 Data memory
204 Communication interface
205 Input/output interface
206 Bus
207 User interface apparatus
2071 Input apparatus
2072 Output apparatus

The invention claimed is:

1. A notification control system, comprising:
a sensor configured to detect movement of a user and generate a movement event in response thereto, where the movement event indicates that the user has moved;
a notification control apparatus comprising:
a processor; and
a storage medium having computer program instructions stored thereon, when executed by the processor, perform to:
receive the movement event from the sensor;
generate a timestamp in response to receiving the movement event and associating the timestamp with the movement event;
determine whether or not the user has a schedule following or preceding the movement event using the timestamp associated with the movement event;
generates an advice to be notified to the user on the basis of the determination and the timestamp associate with the movement event; and
presents the generated advice to the user.

2. The notification control system according to claim 1, wherein the computer program instructions further perform to
determines that the user has a schedule when a value of a schedule presence/absence function that is a function of time is equal to or larger than a predetermined threshold at the occurrence time point of the movement event but determines that the user does not have a schedule when the value is smaller than the predetermined threshold, and
the schedule presence/absence function is a function for determining whether or not the user has a schedule immediately following or immediately preceding the movement event and the schedule presence/absence function has a gamma distribution-like shape having peaks at a plurality of times.

3. The notification control system according to claim 2, wherein when the movement event is an out-event including leaving a seat of the user or leaving a room in which the user is present, the peak of the schedule presence/absence function appears within a prescribed number of minutes preceding every hour or every half hour which is not included in a set schedule-free time slot, and when the computer program instructions determines that the user does not have a schedule, the computer program instructions further perform to message generation unit generates an advice to be notified to the user.

4. The notification control system according to claim 2, wherein when the movement event is an in-event including sitting on a seat of the user or entering the user's room, the peak of the schedule presence/absence function appears within a prescribed number of minutes following every hour or every half hour which is not included in a set schedule-free time slot, and when the computer program instructions determines that the user does not have a schedule, the computer program instructions further perform to generates an advice to be notified to the user.

5. The notification control system apparatus according to claim 2, wherein
when the movement event is an in-event including sitting on a seat of the user or entering the user's room, the peak of the schedule presence/absence function appears within a prescribed number of minutes following every hour or every half hour which is not included in a set schedule-free time slot, wherein the computer program instructions further perform to
determines whether or not to notify the user of the advice according to a presence or an absence of a schedule of the user as determined by the schedule presence/absence determination unit, and when determines that the user is to be notified of the advice, generates the advice to be notified to the user.

* * * * *